United States Patent [19]

Solenberger

[11] Patent Number: 5,673,693

[45] Date of Patent: Oct. 7, 1997

[54] METHOD AND APPARATUS FOR IMPROVING THE DURABILITY OF A SENSOR

[75] Inventor: Stephen D. Solenberger, Glen Moore, Pa.

[73] Assignee: Medical Taping Systems, Inc., Glen Moore, Pa.

[21] Appl. No.: 505,975

[22] Filed: Jul. 24, 1995

Related U.S. Application Data

[62] Division of Ser. No. 172,477, Dec. 23, 1993, Pat. No. 5,507,286.

[51] Int. Cl.$^6$ ........................................................ A61B 5/00
[52] U.S. Cl. ............................................................ 128/633
[58] Field of Search ............................ 128/633, 664–667, 128/686; 356/39–41; 206/305, 306

[56] References Cited

U.S. PATENT DOCUMENTS

| 4,621,643 | 11/1986 | New, Jr. et al. | 128/633 |
| 4,700,708 | 10/1987 | New, Jr. et al. | 128/633 |
| 4,830,014 | 5/1989 | Goodman et al. | 128/665 |
| 4,865,038 | 9/1989 | Rich et al. | 128/633 |
| 5,090,410 | 2/1992 | Saper et al. | 128/633 |

OTHER PUBLICATIONS

Datascope Flexisensor SD Advertisement, 0061–00–0312 0389, Copyright 1989 Datascope Corp, Paramus, NJ.
The Nellcor Sensor Advantage Advertisement, Nellcor Incorporated, Hayward, CA.

Vida Racys, M.D. and Michael L. Nahrwold, M.D., "Reusing the Nellcor Pulse Eximeter Probe: Is it worth the Savings?", *Anesthesiology*, 66:7 13, 1987.

M.S. Read, MD, "Effect of Transparent Adhesive Tape on Pulse Oximetry", *Anesthesia and Analgesia*, vol. 68, pp. 701–2, 1989.

Morris Shlamowitz and Rafael Miguel, MD, "Prolonging the Lifespan of Disposable Nellcor Pulse Oxisensors", *Journal of Clinical Monitoring*, vol. 6, No. 2, Apr., 1990.

James A. Tharp, MD, "A Cost–Saving Method of Modifying the Nellcor® Pulse Oximeter Finger Probe", *Anesthesiology*, 65:446, 1986.

Garfield B. Russell, MD and John M. Graybeal CRTT, "Accuracy of Laminated Disposable Pulse–Oximeter Sensors", *Respiratory Care*, vol. 40, No. 7, Jul., 1995.

R. J. Santerelli, D. Gerber, W.E. Scott, M.E. Kern, J. DuBois, "Evaluation of a Protective Sheath for Disposable Pulse Oximetry Probes: Effect on Oxygen Saturation Determinations", Poster Reproduction from American College of Chest Physicians, Oct. 30–Nov. 3, 1994.

*Primary Examiner*—Angela D. Sykes
*Assistant Examiner*—Eric F. Winakur
*Attorney, Agent, or Firm*—Roland B. Desilets

[57] ABSTRACT

The present invention relates to a method and apparatus for improving the durability of a sensor, specifically one attached by an adhesive material to a subject. Specifically, the present invention discloses a method and apparatus for laminating a sensor and inserting the sensor into a protective shield for use. The shield includes some adhesive material to affix the sensor to the subject. A dirty, damaged, or worn out shield may be discarded and the sensor inserted into a new shield for continued use of the sensor.

4 Claims, 3 Drawing Sheets

METHOD AND APPARATUS FOR IMPROVING THE DURABILITY OF A SENSOR

This application is a division of application Ser. No. 8,172,477, filed Dec. 23, 1993, now U.S. Pat. No. 5,507,286.

FIELD OF THE INVENTION

The present invention relates to the field of sensors which are attached to a subject to be monitored, particularly a sensor which is attached with adhesive to the subject. The preferred embodiment of the present invention is directed to the field of sensors for use with pulse oximeters.

BACKGROUND OF THE INVENTION

The present invention provides a means of improving the durability of a sensor, particularly a sensor which is attached with adhesive to the subject which is to be monitored. The preferred embodiment of the present invention is directed to improving the durability of sensors which are connected to pulse oximeters.

A pulse oximeter is a device which monitors the oxygen content of the blood of a subject by measuring the blood's absorption of light. The sensor includes a pair of light emitting diodes (L.E.D.) and a photocell detector which are coupled to wires connected to the pulse oximeter. The diodes, the detector, and a portion of the wires are covered with a flexible casing made of plastic and paper. An adhesive material is typically coupled to the casing.

When in use, the casing is wrapped around a part of the subject, typically a finger. When properly applied, the diodes are aligned on the subject so that they are facing the photocell detector with the subject's finger in between. The sensor is held in this position by affixing it to the skin with the adhesive material.

A known problem with the sensors described above is the limited lifespan of the adhesive and the lack of durability of the casing.

In addition, maintaining the cleanliness of the sensor is desirable since the casing touches the skin of the subject directly. However, the ability to clean the sensor is limited in that the adhesive portion of the sensor is permanently coupled to the casing. The adhesive portion cannot be conveniently cleaned without adversely affecting the strength of the remaining adhesive.

Another motivation for making such cleaning possible is to maintain the accuracy of the sensor. A study has shown that a build up of adhesive on the diodes may cause inaccurate readings by the pulse oximeter. Inaccurate readings on a medical instrument are clearly undesirable and potentially dangerous. The ability to clean the diodes and detector would provide a means to avoid this potential source of inaccuracy, potentially increasing patient safety.

SUMMARY AND OBJECT OF THE INVENTION

It is an object of the present invention to increase the durability of a sensor.

It is a further object of the present invention to make convenient cleaning of a sensor possible without adversely affecting the function of the sensor.

It is another object of the present invention to improve the cleanliness of a sensor by providing a dedicated means of attaching the sensor to the subject.

It is yet a further object of the present invention to provide a uniform size shield to protect and affix a variety of sensors of potentially different sizes.

It also an object of the present invention to provide all of the above objects without adversely affecting the performance of the sensor during use.

The method of the present invention involves laminating the casing of the sensor to increase its durability. The lamination material includes two apertures; one to accommodate the diodes and one to accommodate the detector.

The laminated casing may then be inserted into a disposable shield which includes an adhesive strip. The shield protects the casing of the sensor from direct contact with the subject's skin. In the preferred embodiment, the shape of the shield is well suited to the proper mounting of the sensor on the subject's finger. However, the shield may be of other shapes and configurations to facilitate mounting on a toe or some other extremity, as appropriate.

The use of the present invention permits the laminated casing to be easily removed from the shield and the shield to be discarded. The laminated casing may be cleaned and inserted into a new clean shield for use. In this way, conditions that may have previously been cause for discarding the sensor are now only cause for discarding the shield. Examples of such occurrences are contamination of the shield, loss of adhesion of the adhesive, tearing or other damage to the adhesive material portion.

The foregoing and other objects features and advantages of the present invention will be apparent from the following, more particular description of the preferred embodiment of the invention and as illustrated in the accompanying drawings.

DETAILED DESCRIPTION

Figure 1:
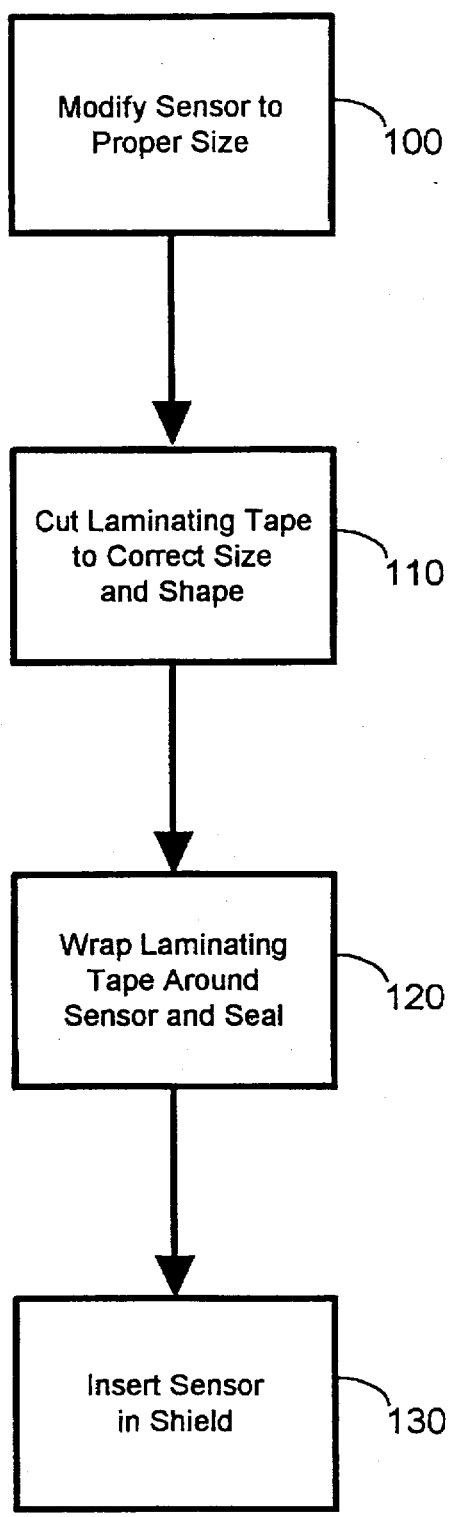
FIG. 1 illustrates the steps involved in improving a sensor with the present invention.

The present invention permits a sensor to be improved for durability and cleanliness. The steps employed to modify a sensor for use in the preferred embodiment are described with reference to FIG. 1.

First, the sensor is prepared for lamination 100, which often involves physical modification to the sensor. This modification may involve making the profile of the casing larger or smaller, as appropriate. In a preferred embodiment, this involves removing some or all of the adhesive material from the casing by trimming or tearing it away. An alternative embodiment may include modifying the sensor make it the appropriate shape for later insertion into the shield.

Next, the laminating tape is cut to the appropriate size and shape for the shape of sensor 110 and for the size of the shield in which the sensor shall be inserted. In the preferred embodiment, the commercially available laminating tape employed is a polyethylene wrap with a tape seal at each end. Employing a clear laminating tape facilitates use of the sensor by leaving identifying marks or other information printed on the casing visible to the user. The thickness of the laminating tape may be varied to improve durability of the sensor or to facilitate the proper fit of the laminated sensor in the shield.

In the preferred embodiment for use with pulse oximeter sensors, two apertures are made at the appropriate locations on the laminating tape for alignment with the diodes and the detector of the sensor. For example, if the commercially available D-25 sensor sold by Nellcor is employed, these apertures are made 25 mm apart to properly align with the diodes and detector on the sensor when the sensor is laminated.

The laminating tape is wrapped around the sensor, folded over and sealed securely 120. In the preferred embodiment, the laminating tape is wrapped such that each aperture lines up properly with a respective diode or detector, as appropriate.

The laminated sensor may now be inserted into the shield 130. In the preferred embodiment, the shield is comprised of a polyethylene plastic sleeve which is coupled to a segment of adhesive material which has been properly cut to shape for its intended use. The sleeve is of a sufficient diameter to accommodate the sensor to be employed. Preferably, the sleeve will be of a size to accommodate a number of different type sensors for use with a single type of shield.

In the preferred embodiment, the adhesive tape employed is a commercially available moisture vapor transmission tape. As with the laminating material, the use of a clear material facilitates use of the sensor by leaving identifying marks or alignment marks or other information printed on the casing of the sensor visible to the user. It also leaves visible the portion of the subject's skin to which the sensor is attached.

Figure 2:
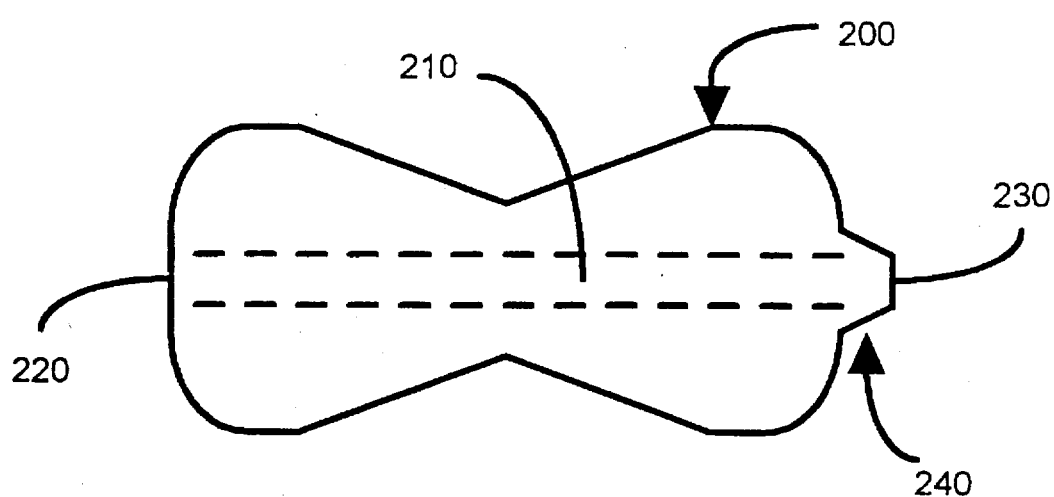
FIG. 2 illustrates in the adhesive shield employed in the preferred embodiment of the present invention.

In the preferred embodiment, the adhesive tape is cut to a shape as detailed in FIG. 2 for attachment to a subject's finger. Other shapes may be appropriate for another use, such as attachment to a toe.

Upon completion of the above steps, the sensor is ready to be attached to the subject, as appropriate. If the shield becomes damaged or dirty, or the adhesive loses its strength, the old shield may be discarded and replaced with a new clean shield. When performing such replacement, it may also be desirable to clean the sensor before inserting the sensor in the shield. This may be done with an antiseptic, such as by an alcohol wipe.

With reference now to FIG. 2, the adhesive shield employed with the present invention will now be described. Adhesive tape 200 is cut to facilitate attachment to the subject. FIG. 2 shows a possible set of dimensions for the adhesive tape 200 for use in the preferred embodiment, which is for attachment to a subject's finger.

The location of the plastic sleeve 210, although not its actual dimension, is shown with a dotted line down the lengthwise portion of the adhesive material 200. The sleeve may be sealed at one end 220, although in a preferred embodiment, it is not. The opposite end 230 of the shield is used to insert the casing of the sensor into the sleeve 210 for use. The adhesive material is cut to include a tab 240 to facilitate the opening of the sleeve 210 and insertion of the sensor.

Figure 3:
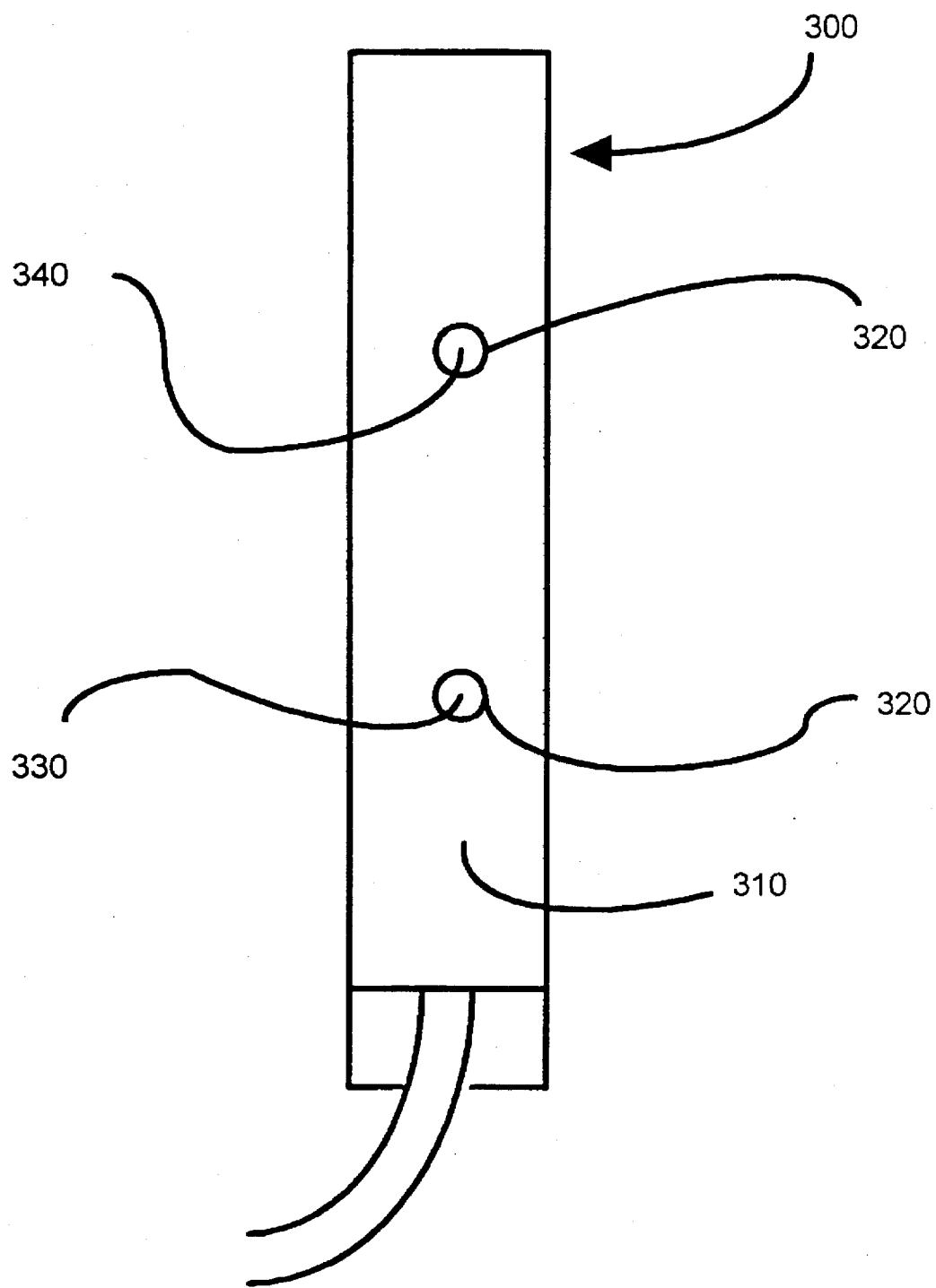
FIG. 3 illustrates the surface of a sensor employed in the preferred embodiment of the present invention.

With reference now to FIG. 3, the appearance of the surface of the laminated sensor will now be described. The laminating tape 300 is wrapped around the length of the sensor casing 310 and folded over to seal both ends. Apertures 320 are cut into the laminating tape 300 of the appropriate width and at the appropriate location such that they will align with the diodes 330 and the photocell detector 340 when the laminating tape is applied to the sensor casing 310.

Some of the many advantages of the present invention should now be readily apparent. For example, the sensor thus laminated and employed with a series of shields may continue to be used as long as reliable readings are obtained by the sensor.

Obviously, many modifications and variations of the present invention are possible in light of the above teachings. For instance, sensors for devices other than pulse oximeters which employ adhesive to attach to a subject may advantageously employ this invention. In addition, pulse oximeters which employ sensors that attach to other parts of a subject, such as a toe, may also employ this invention. It is therefore to be understood that the foregoing embodiments are presented by way of example only and that within the scope of the claims attached hereto the invention may be practiced other than as specifically described.

What is claimed:

1. An improvement to a sensor for use with a pulse oximeter, wherein said sensor includes at least one light emitting diode and at least one photocell detector, comprising:

a) laminating material, including a first aperture at least as large as said diode and a second aperture at least as large as said detector, wherein said laminating material enwraps said sensor and said first aperture is homologously aligned with said diode and said second aperture is homologously aligned with said detector;

b) sleeve, into which said laminated sensor is inserted;

c) adhesive means, coupled to the exterior of said sleeve, for attaching said sensor to a subject;

wherein said laminating material includes a tape seal at each end.

2. The apparatus of claim 1 wherein said laminating material comprises a clear polyethylene wrap.

3. The apparatus of claim 1 wherein said adhesive means for attaching said sensor to a subject comprises a clear moisture vapor transmission tape.

4. The apparatus of claim 1 wherein said adhesive means for attaching said sensor to a subject includes a tab.

* * * * *